US00PP23291P2

(12) United States Plant Patent
Ackerman et al.

(10) Patent No.: US PP23,291 P2
(45) Date of Patent: Jan. 1, 2013

(54) STRAWBERRY PLANT NAMED 'PS-3.108'

(50) Latin Name: *Fragaria ananassa*
Varietal Denomination: PS-3.108

(75) Inventors: Stephen M. Ackerman, Salinas, CA (US); Steven D. Nelson, Watsonville, CA (US); Michael D. Nelson, Watsonville, CA (US)

(73) Assignees: Berry R&D, Inc., Watsonville, CA (US); Plant Sciences, Inc., Watsonville, CA (US)

( * ) Notice: Subject to any disclaimer, the term of this patent is extended or adjusted under 35 U.S.C. 154(b) by 0 days.

(21) Appl. No.: 13/137,804

(22) Filed: Sep. 14, 2011

(51) Int. Cl.
*A01H 5/00* (2006.01)

(52) U.S. Cl. ..... Plt./209

(58) Field of Classification Search ..... Plt./209
See application file for complete search history.

*Primary Examiner* — Annette Para
(74) *Attorney, Agent, or Firm* — Foley & Lardner LLP

(57) ABSTRACT

This invention relates to a new and distinct variety of strawberry plant named 'PS-3.108'. This new strawberry plant named 'PS-3.108' is primarily adapted to the growing conditions of the central coast of California, and is primarily characterized by its dark red to red fruit color, large to very large fruit size, medium plant vigor, conical fruit shape, firm fruit flesh, and early fruit ripening.

4 Drawing Sheets

Latin name of the genus and species of the plant claimed: *Fragaria ananassa.*

Variety denomination: 'PS-3.108'.

BACKGROUND OF THE INVENTION

The present invention relates to a new and distinct strawberry variety named 'PS-3.108'. This new variety is a result of a controlled cross made in 2003 in an ongoing breeding program between strawberry variety designated 'PS-1269' (patented, U.S. Plant Pat. No. 10,686) and strawberry variety designated 'PS-4634' (patented, U.S. Plant Pat. No. 17,487). Due to the combining of the reciprocal seed lots, it is unknown as to which parent variety is the seed parent and which parent variety is the pollen parent. The variety is botanically known as *Fragaria ananassa.*

The seedling resulting from the aforementioned cross was selected from a controlled breeding plot in Monterey County, Calif. in the summer of 2005. After its selection, the new variety was asexually propagated by stolons in both San Joaquin County, Calif. and Siskiyou County, Calif. The new variety was extensively tested over the next several years in fruiting fields in Monterey County, Calif. This propagation has demonstrated that the combination of traits disclosed herein as characterizing the new variety are fixed and remain true to type through successive generations of asexual reproduction.

BRIEF SUMMARY OF THE INVENTION

'PS-3.108' is primarily adapted to the climate and growing conditions of the central coast of California. The nearby Pacific Ocean provides the needed humidity and moderate temperatures to produce a strong vigorous plant and maintain fruit quality during the April through November production months.

The following traits have been repeatedly observed and are determined to be unique characteristics of 'PS-3.108', which in combination distinguish this strawberry plant as a new and distinct variety:

1. Dark red to red fruit color;
2. Large to very large fruit size;
3. Medium plant vigor;
4. Conical fruit shape;
5. Firm fruit flesh; and
6. Early fruit ripening The strawberry variety that is believed to be most closely related to the new variety 'PS-3.108' is 'PS-4634' (patented, U.S. Plant Pat. No. 17,487). In side-by-side comparisons to the similar strawberry variety 'PS-4634', 'PS-3.108' differs by the following combination of characteristics as described in Table 1.

TABLE 1

COMPARISON TO THE STANDARD VARIETY

| Characteristic | 'PS-3.108' | 'PS-4634' (U.S. Plant Pat. No. 17,487) |
|---|---|---|
| Fruit color | Ranges from red to dark red | Ranges from orange red to red |
| Average marketable yield | 1,969 grams/plant | 1,689 grams/plant |
| Difference in shape between primary and secondary fruit | Ranges from none to very slight | Moderate |
| Size of calyx in relationship to fruit diameter | Slightly larger | Same size |
| Firmness of flesh | Firm | Medium |
| Expression of hollow center | Weak | Strong |
| Plant size | Medium | Large |
| Foliage color | Ranges from light to medium yellow green | Medium green |
| Foliage shape in cross section | Ranges from lightly to strongly concave | Ranges from lightly concave to flat |

For identification, a series of molecular markers have been determined for this new variety.

'PS-3.108' differs from its parents, 'PS-1269' and 'PS-4634' by the following combination of characteristics as described in Table 2.

TABLE 2

COMPARISON TO THE PARENT VARIETIES

| Characteristic | 'PS-3.108' | 'PS-1269' (U.S. Plant Pat. No. 10,686) | 'PS-4634' (U.S. Plant Pat. No. 17,487) |
|---|---|---|---|
| Fruit color | Ranges from red to dark red | Red | Ranges from orange red to red |
| Average marketable yield | 1,969 grams/plant | 1,443 grams/plant | 1,689 grams/plant |
| Difference in shape between primary and secondary fruit | Ranges from none to very slight | Ranges from moderate to marked | Moderate |
| Fruit gloss | Medium | Ranges from weak to medium | Strong |

BRIEF DESCRIPTIONS OF THE PHOTOGRAPHS

The accompanying color photographs illustrate the overall appearance of typical specimens of the new strawberry variety 'PS-3.108', at various stages of development as true as it is reasonably possible with color reproductions of this type. Color in the photographs may differ slightly from the color value cited in the botanical descriptions which accurately describe the color of 'PS-3.108'. The depicted plant and plant parts of the new strawberry variety 'PS-3.108' are between eight and nine months old. The photographs were taken in Monterey County, Calif.:

DETAILED BOTANICAL DESCRIPTION

Figure 1:
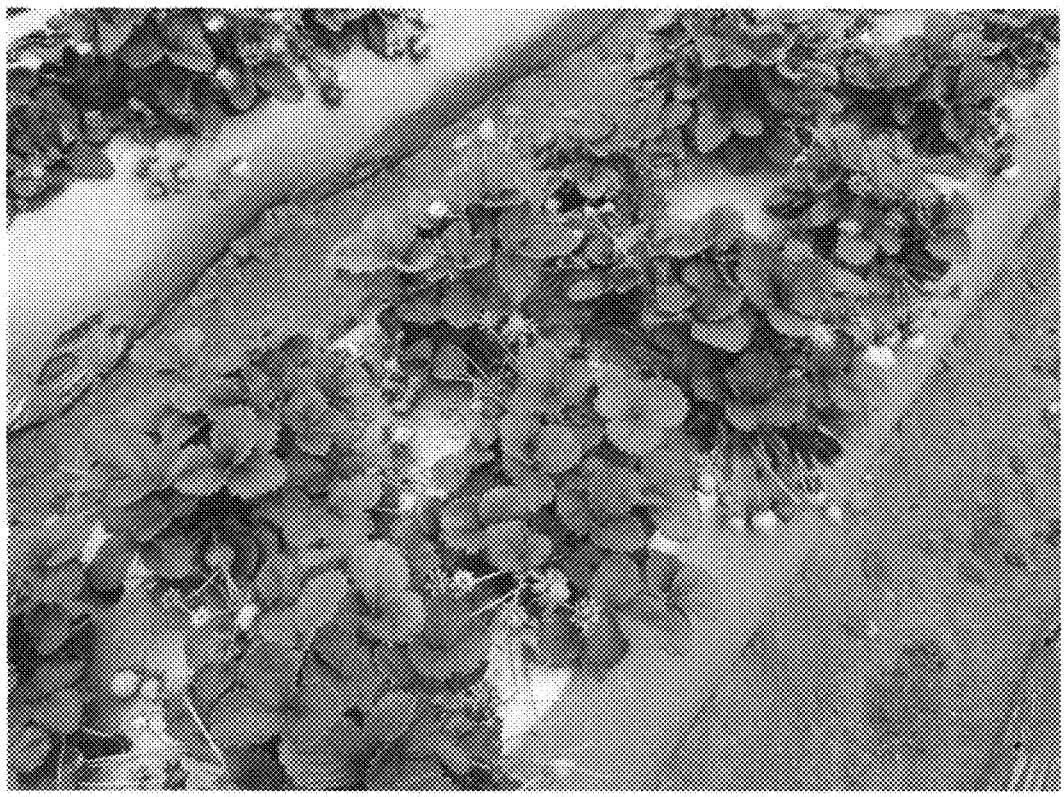
FIG. 1 shows typical fruiting field characteristics of 'PS-3.108', taken in the month of July 2011.
Figure 2:
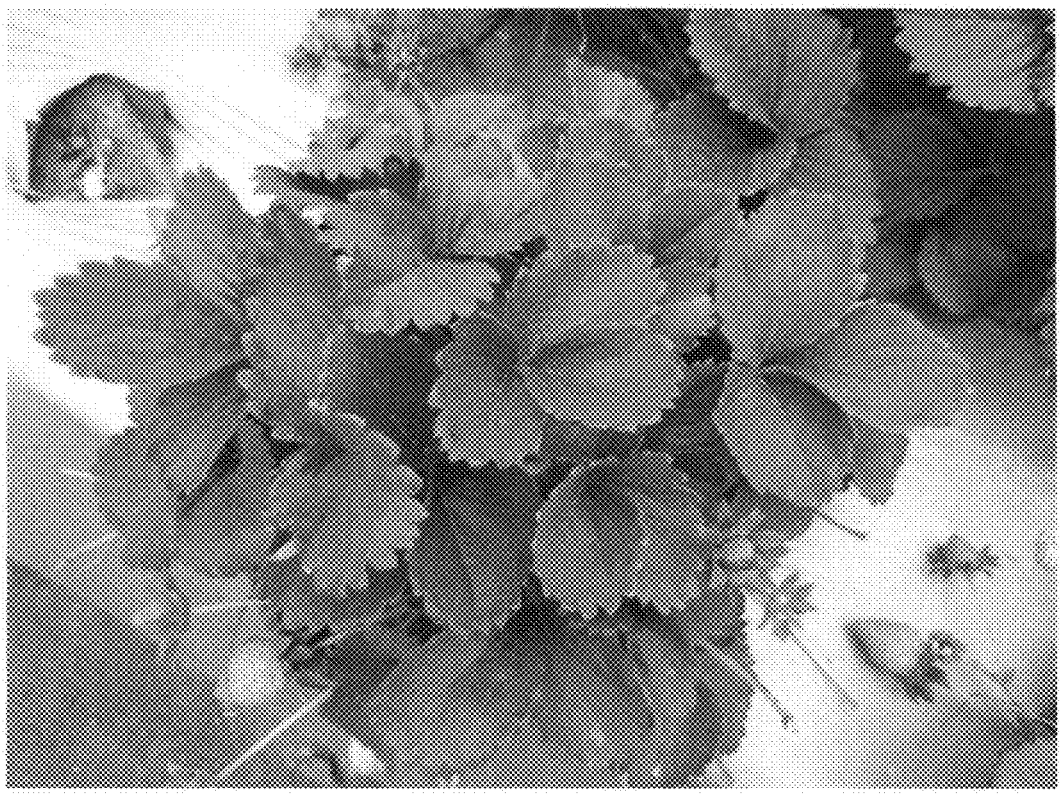
FIG. 2 shows a close-up view of the typical leaf structure of 'PS-3.108', taken in the month of July 2011.
Figure 3:
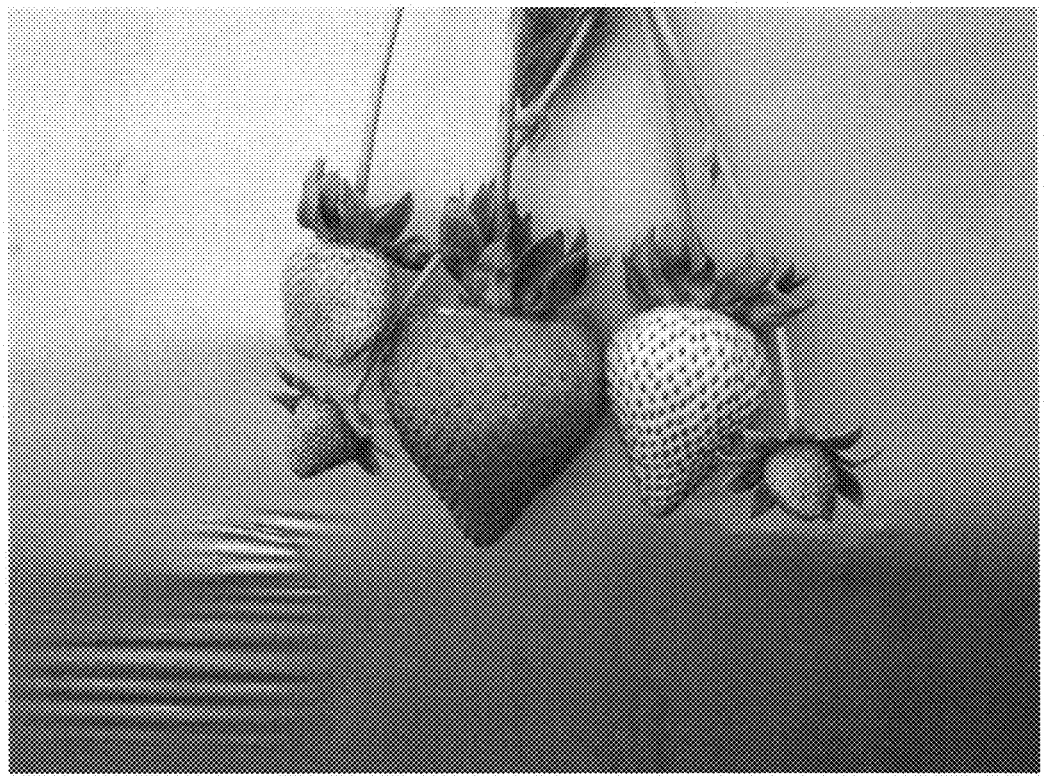
FIG. 3 shows typical mature and immature field fruit of 'PS-3.108', taken in the month of July 2011.
Figure 4:
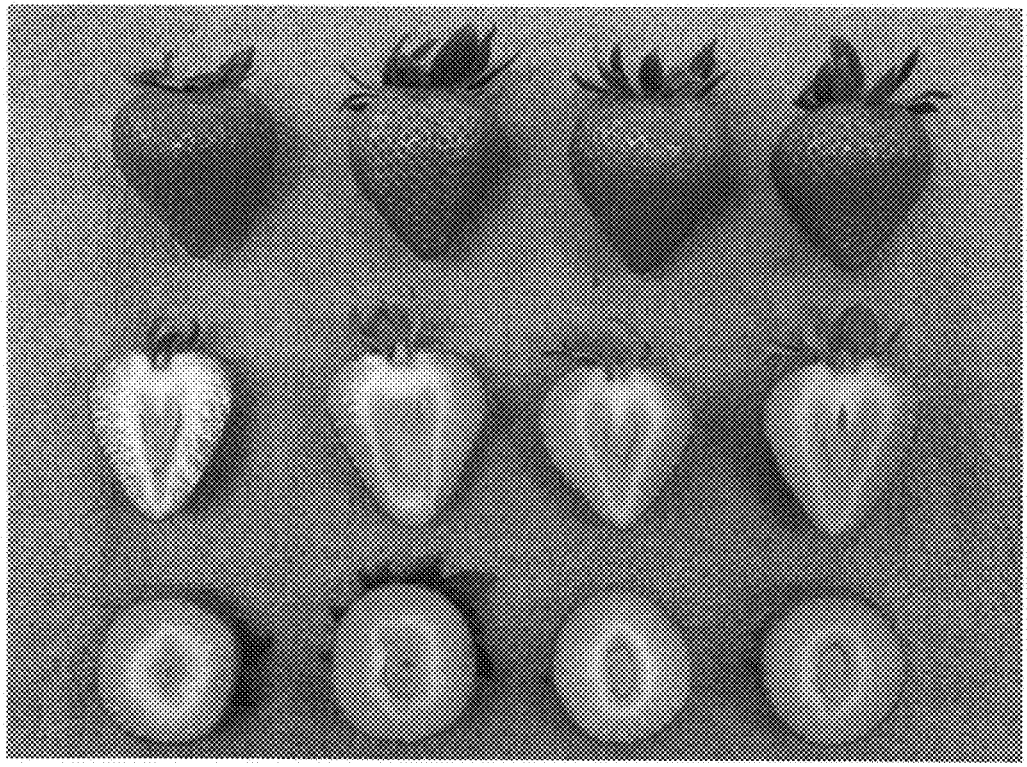
FIG. 4 shows typical internal and external mature fruit characteristics of 'PS-3.108', taken in the month of August 2011.

The new variety 'PS-3.108' has not been observed under all possible environmental conditions. The characteristics of the new variety 'PS-3.108' may vary in detail, depending upon variations in environmental factors, including weather (temperature, humidity and light intensity), day length, soil type and location. In addition, the characteristics of any parental variety or comparison variety included in Tables 1-9 of the present invention may vary in detail, depending upon variations in environmental factors, including weather (temperature, humidity and light intensity), day length, soil type and location.

The aforementioned photographs, together with the following description of the new variety 'PS-3.108', unless otherwise noted, are based on observations taken during the 2011 growing season in Monterey County, Calif. These measurements and ratings were taken from plants of 'PS-3.108' dug from a high-elevation nursery located in Siskiyou County, Calif. during mid October 2010 and planted between two and three weeks later in Monterey County, Calif. The approximate age of the observed plants is between eight and nine months. Yield observations and fruit quality characteristics are averaged from three years of data collected from the 2008 through 2010 growing seasons. Flower measurements and characteristics are from secondary flowers unless otherwise noted. Fruit characteristics and measurements are from secondary fruit unless otherwise noted.

Color terminology where noted follows The Royal Horticultural Society Colour Chart, London (2007).

The following tables 3 through 9 describe fruit, plant, stolon, foliage, fruiting truss, flower and pest disease characteristics of the new strawberry 'PS-3.108' in comparison to the similar strawberry variety 'PS-4634'.

TABLE 3

FRUIT CHARACTERISTICS

| Characteristic | 'PS-3.108' | 'PS-4634' (U.S. Plant Pat. No. 17,487) |
|---|---|---|
| Color of mature fruit | RHS 46A Ranges from red to dark red | RHS 45B Ranges from orange red to red |
| Color of internal flesh | RHS 44B Medium red | RHS 44C Ranges from light red to medium red |
| Fruit length (cm) | 4.5 | 4.3 |
| Fruit width (cm) | 3.8 | 3.9 |
| Fruit length/width ratio | 1.17 Slightly longer than broad | 1.11 Slightly longer than broad |
| Calyx diameter (cm) | 4.2 | 4.0 |
| Average fruit weight (gm) | 29.6 | 27.7 |
| Achene color, shaded side | RHS 162B Greyed yellow group | RHS 162C Greyed yellow group |
| Achene color, sun-exposed side | RHS 184B Greyed purple group | RHS 184C Greyed purple group |
| Achenes per berry | 438 | 437 |
| Achene weight (mg) | 0.52 | 0.40 |
| Marketable fruit yield (gm/plant) | 1,969 | 1,689 |
| Fruit size | Ranges from large to very large | Ranges from large to very large |
| Predominant fruit shape | Conical | Conical |
| Difference in shapes between primary and secondary fruit | None or very slight | Moderate |
| Band without achenes | Absent or very narrow | Narrow |
| Unevenness of fruit surface | Absent or very weak | Weak |
| Evenness of fruit color | Even | Ranges from slightly uneven to even |
| Fruit glossiness | Medium | Strong |
| Insertion of achenes | Level with surface | Level with surface |
| Insertion of calyx | In basin | Ranges from in basin to level |
| Attitude of calyx | Spreading | Ranges from spreading to reflexed |
| Size of calyx in relation to fruit diameter | Slightly larger | Same size |
| Adherence of calyx | Strong | Strong |
| Firmness of fruit skin | Strong | Strong |
| Firmness of fruit flesh | Firm | Medium |
| Keeping quality | Very good | Very good |
| Distribution of red color of the flesh | Marginal and central | Marginal and central |
| Hollow center expression | Weak | Strong |
| Fruit flavor | Good | Very good |
| Soluble solids (% brix) | 7.4 | 8.3 |
| Time of first flowering | Early | Early |
| Time of first harvesting | Early | Early |
| Harvest period | Late March to November | Late March to November |
| Type of bearing | June bearing | June bearing |

TABLE 4

| PLANT CHARACTERISTICS | | |
|---|---|---|
| Characteristic | 'PS-3.108' | 'PS-4634' (U.S. Plant Pat. No. 17,487) |
| Plant height (cm) | 25.3 | 28.8 |
| Plant spread (cm) | 33.9 | 39.1 |
| Plant size | Medium | Large |
| Plant habit | Globose | Globose |
| Plant density | Medium | Medium |
| Plant vigor | Medium | Strong |

TABLE 5

| STOLON CHARACTERISTICS | | |
|---|---|---|
| Characteristic | 'PS-3.108' | 'PS-4634' (U.S. Plant Pat. No. 17,487) |
| Stolon color | RHS 146D Yellow green group | RHS 146D Yellow green group |
| Stolon anthocyanin coloration | RHS 182A Greyed red group | RHS 182D Greyed red group |
| Stolon anthocyanin intensity | Weak | Ranges from weak to medium |
| Stolon pubescence | Medium | Ranges from weak to medium |
| Attitude of hairs | Upward | Upward |
| Average stolon quantity | Ranges from medium to many | Ranges from medium to many |
| Stolon diameter at bract (mm) | 3.7 | 3.4 |

TABLE 6

| FOLIAGE CHARACTERISTICS | | |
|---|---|---|
| Characteristic | 'PS-3.108' | 'PS-4634' (U.S. Plant Pat. No. 17,487) |
| Foliage: | | |
| Color of upper surface | RHS 146A Ranges from light yellow green to medium yellow green | RHS 137A Medium green |
| Color of underside | RHS 147C Yellow green group | RHS 147C Yellow green group |
| Number of leaflets | 3 | 3 |
| Shape in cross section | Strongly to slightly concave | Slightly concave to flat |
| Interveinal blistering | Ranges from medium to strong | Ranges from medium to strong |
| Leaf glossiness | Ranges from medium to strong | Ranges from medium to strong |
| Terminal Leaflet: | | |
| Length (cm) | 8.5 | 9.5 |
| Width (cm) | 7.7 | 6.9 |
| Leaf size | Ranges from large to medium | Ranges from large to medium |
| Length/width ratio | 1.11 Longer than broad | 1.36 Much longer than broad |
| Shape of base | Obtuse | Acute |
| Shape of teeth | Obtuse | Obtuse |
| Serrations per leaf | 18.7 | 22.1 |
| Petiole: | | |
| Petiole color | RHS 145A Yellow green group | RHS 145A Yellow green group |
| Petiole length (cm) | 15.6 | 20.2 |
| Petiole diameter (mm) | 4.0 | 4.4 |
| Petiolule color | RHS 145A Yellow green group | RHS 145A Yellow green group |

TABLE 6-continued

| FOLIAGE CHARACTERISTICS | | |
|---|---|---|
| Characteristic | 'PS-3.108' | 'PS-4634' (U.S. Plant Pat. No. 17,487) |
| Petiolule length (mm) | 9.7 | 7.8 |
| Attitude of hairs | Strongly outward | Strongly outward |
| Petiole pubescence | Moderate | Ranges from moderate to sparse |
| Stipule: | | |
| Color | RHS 146B Yellow green group | RHS 146B Yellow green group |
| Anthocyanin coloration | RHS 63A Red purple group | RHS 58A Red purple group |
| Anthocyanin intensity | Strong | Strong |
| Length (mm) | 18.1 | 18.7 |
| Width (mm) | 9.9 | 8.3 |

TABLE 7

| FRUITING TRUSS CHARACTERISTICS | | |
|---|---|---|
| Characteristic | 'PS-3.108' | 'PS-4634' (U.S. Plant Pat. No. 17,487) |
| Anthocyanin coloration | RHS 181C Greyed red group | RHS 182D Greyed red group |
| Anthocyanin intensity | Absent or very weak | Absent or very weak |
| Length at maturity (cm) | 29.5 | 35.3 |
| Position relative to foliage | Level with | Level with |
| Pubescence | Medium | Ranges from weak to medium |
| Attitude at first pick | Prostrate | Prostrate |

TABLE 8

| FLOWER CHARACTERISTICS | | |
|---|---|---|
| Characteristic | 'PS-3.108' | 'PS-4634' (U.S. Plant Pat. No. 17,487) |
| Petal color | RHS NN 155C White group | RHS NN 155C White group |
| Sepal color | RHS 137C Green group | RHS 137A Green group |
| Corolla diameter (mm) | 26.3 | 29.9 |
| Calyx diameter (mm) | 36.5 | 35.7 |
| Petal length (mm) | 11.3 | 12.3 |
| Petal width (mm) | 12.0 | 12.5 |
| Petal length/width ratio | 0.94 | 0.98 |
| Petals/flower | 6.8 | 5.6 |
| Sepal length (mm) | 13.9 | 12.8 |
| Sepal width (mm) | 5.8 | 5.2 |
| Sepal length/width ratio | 2.40 | 2.46 |
| Sepals/flower | 13.7 | 11.3 |
| Size of calyx relative to corolla | Larger | Larger |
| Size of inner calyx relative to outer calyx | Ranges from smaller to same | Ranges from same to larger |
| Relative position of petals | Overlapping | Overlapping |

TABLE 9

| PEST AND DISEASE REACTIONS | | |
|---|---|---|
| Characteristic | 'PS-3.108' | 'PS-4634' (U.S. Plant Pat. No. 17,487) |
| Powdery mildew | Moderate | Moderately resistant |
| Angular leaf spot | Susceptible | Susceptible |
| Botrytis fruit rot | Moderately susceptible | Moderately susceptible |
| Two-spotted spider mite | Moderately susceptible | Moderately susceptible |

TABLE 9-continued

| PEST AND DISEASE REACTIONS | | |
|---|---|---|
| Characteristic | 'PS-3.108' | 'PS-4634' (U.S. Plant Pat. No. 17,487) |
| Lygus bug | Susceptible | Susceptible |
| Flower thrips | Moderately resistant | Moderately susceptible |

We claim:

1. A new and distinct strawberry plant named 'PS-3.108', as herein described and illustrated by the characteristics set forth above.

* * * * *

UNITED STATES PATENT AND TRADEMARK OFFICE

CERTIFICATE OF CORRECTION

PATENT NO. : PP23,291 P2
APPLICATION NO. : 13/137804
DATED : January 1, 2013
INVENTOR(S) : Ackerman et al.

It is certified that error appears in the above-identified patent and that said Letters Patent is hereby corrected as shown below:

On the Title Page:

Item (73) "Assignees: Berry R&D, Inc., Watsonville, CA (US); Plant Sciences, Inc., Watsonville, CA (US)"

should be changed to:

(73) --Assignee: Plant Sciences, Inc., Watsonville, CA (US)--

Signed and Sealed this
Tenth Day of May, 2016

Michelle K. Lee

Michelle K. Lee
*Director of the United States Patent and Trademark Office*